US00PP36748P2

(12) United States Plant Patent
Mathey

(10) Patent No.: US PP36,748 P2
(45) Date of Patent: Jun. 17, 2025

(54) ***BUDDLEIA* PLANT NAMED 'SMNBAB'**

(50) Latin Name: *Buddleia alternifolia*
Varietal Denomination: SMNBAB

(71) Applicant: Megan M. Mathey, Holland, MI (US)

(72) Inventor: Megan M. Mathey, Holland, MI (US)

(73) Assignee: Spring Meadow Nursery, Inc., Grand Haven, MI (US)

( * ) Notice: Subject to any disclaimer, the term of this patent is extended or adjusted under 35 U.S.C. 154(b) by 0 days.

(21) Appl. No.: 18/947,510

(22) Filed: Nov. 14, 2024

(51) Int. Cl.
*A01H 6/00* (2018.01)
*A01H 5/02* (2018.01)

(52) U.S. Cl.
USPC ..... Plt./242

(58) Field of Classification Search
USPC ..... Plt./242
CPC ..... A01H 6/00; A01H 5/02
See application file for complete search history.

*Primary Examiner* — Keith O. Robinson
(74) *Attorney, Agent, or Firm* — C. Anne Whealy

(57) ABSTRACT

A new and distinct cultivar of *Buddleia* plant named 'SMNBAB', characterized by its relatively compact, outwardly spreading to weeping plant habit with cascading inflorescences; vigorous growth habit; freely branching habit; dense and bushy appearance; green-colored leaves with silvery green-colored lower surfaces; freely flowering habit; long and dense conical inflorescences with numerous light purple-colored flowers; and good garden performance.

2 Drawing Sheets

Figure 1:
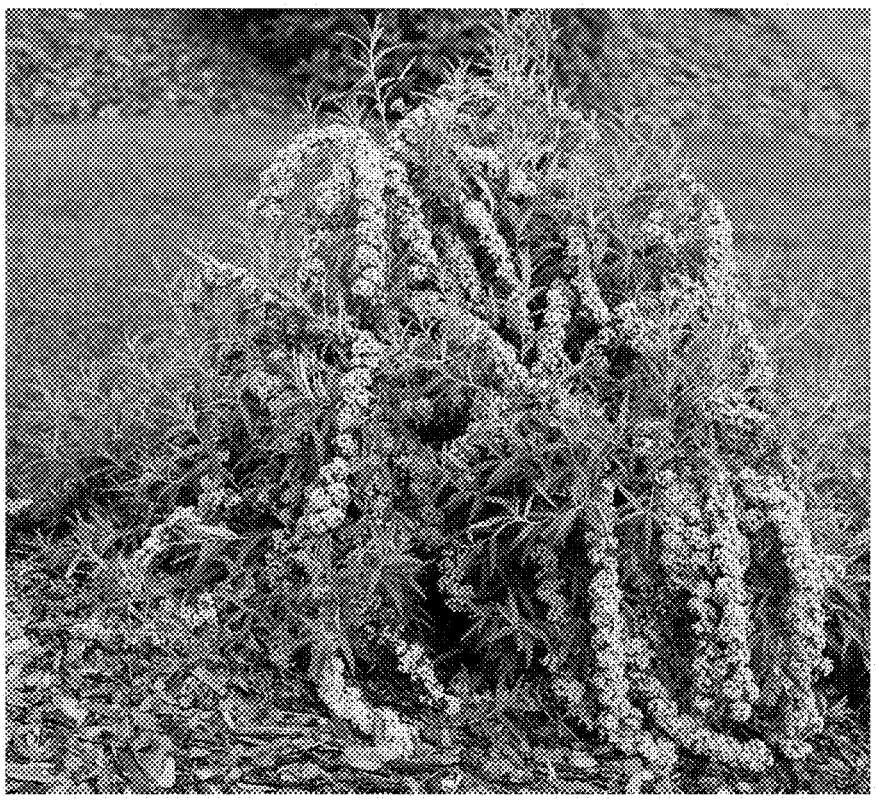

Botanical designation: *Buddleia alternifolia*.
Cultivar denomination: 'SMNBAB'.

BACKGROUND OF THE INVENTION

The present invention relates to a new and distinct *Buddleia* plant, botanically known as *Buddleia alternifolia*, commonly referred to as Alternate-leaf Butterfly Bush and hereinafter referred to by the name 'SMNBAB'.

The new *Buddleia* plant is a product of a planned breeding program conducted by the Inventor in Grand Haven, Michigan. The objective of the breeding program was to create new compact and uniform *Buddleia* plants with weeping habit, cascading inflorescences and attractive leaf and flower coloration.

The new *Buddleia* plant originated from an open-pollination during the summer of 2017 in Grand Haven, Michigan of an unidentified proprietary selection of *Buddleia alternifolia*, not patented as the female, or seed, parent with an unknown selection of *Buddleia alternifolia* as the male, or pollen, parent. The new *Buddleia* plant was discovered and selected by the Inventor as a single flowering plant within the progeny of the stated open-pollination in a controlled environment in Grand Haven, Michigan during the summer of 2020.

Asexual reproduction of the new *Buddleia* plant by softwood stem cuttings in a controlled environment in Grand Haven, Michigan since the summer of 2020 has shown that the unique features of this new *Buddleia* plant are stable and reproduced true to type in successive generations.

SUMMARY OF THE INVENTION

Plants of the new *Buddleia* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNBAB'. These characteristics in combination distinguish 'SMNBAB' as a new and distinct *Buddleia* plant:

1. Relatively compact, outwardly spreading to weeping plant habit with cascading inflorescences.
2. Vigorous growth habit.
3. Freely branching habit; dense and bushy appearance.
4. Green-colored leaves with silvery green-colored lower surfaces.
5. Freely flowering habit.
6. Long and dense conical inflorescences with numerous light purple-colored flowers.
7. Good garden performance.

Plants of the new *Buddleia* differ primarily from plants of the female parent selection in the following characteristics:

1. Plants of the new *Buddleia* are smaller and more compact than plants of the female parent selection.
2. Plants of the new *Buddleia* are more freely branching, denser and more uniform than plants of the female parent selection.
3. Plants of the new *Buddleia* are more freely flowering than plants of the female parent selection.

Plants of the new *Buddleia* can be compared to plants of *Buddleia alternifolia* 'Argentea', not patented. In side-by-side comparisons, plants of the new *Buddleia* differ primarily from plants of 'Argentea' in the following characteristics:

1. Plants of the new *Buddleia* are smaller and more compact than plants of 'Argentea'.
2. Plants of the new *Buddleia* are more freely branching, denser and more uniform than plants of 'Argentea'.
3. Leaves of plants of the new *Buddleia* are green in color with silvery green-colored lower surfaces whereas leaves of plants of 'Argentea' have leaves with silvery green-colored upper and lower surfaces.

BRIEF DESCRIPTION OF THE PHOTOGRAPHS

The accompanying colored photographs illustrate the overall appearance of the new *Buddleia* plant showing the colors as true as it is reasonably possible to obtain in colored reproductions of this type. Colors in the photographs may differ slightly from the color values cited in the detailed botanical description which accurately describe the colors of the new *Buddleia* plant.

The photograph on the first sheet (FIG. 1) is a side perspective view of a typical flowering plant of 'SMNBAB' grown in an outdoor nursery.

Figure 2:
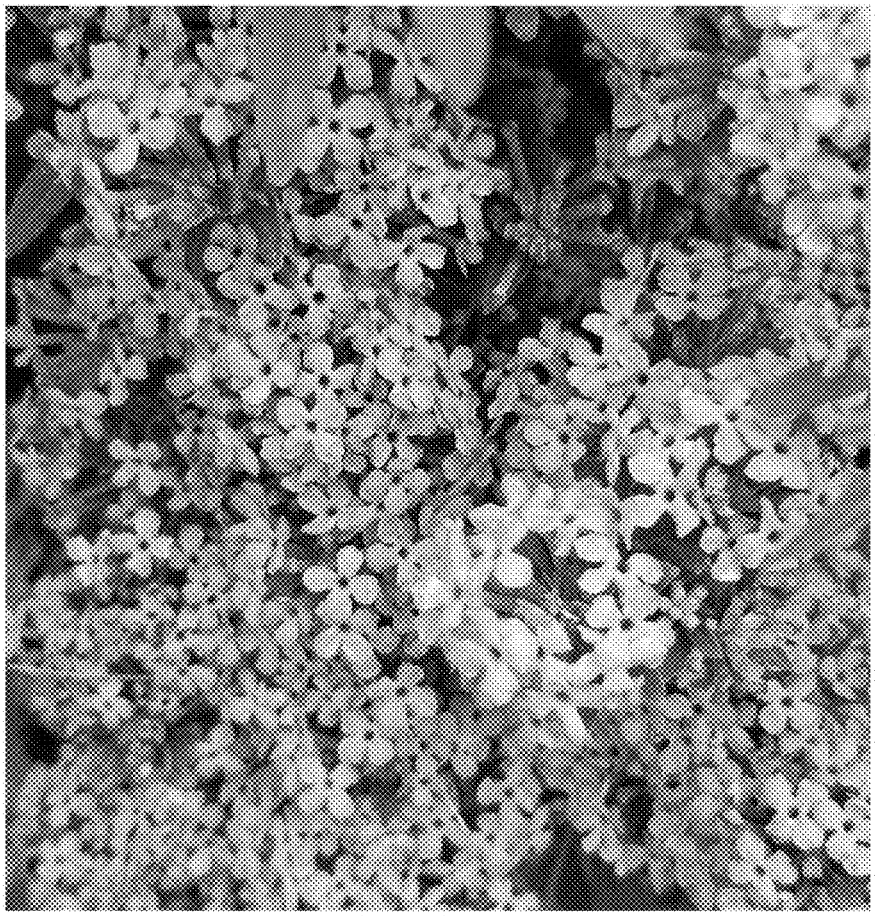

The photograph on the second sheet (FIG. 2) is a close-up view of a typical flowering plant of 'SMNBAB'.

DETAILED BOTANICAL DESCRIPTION

The following observations, measurements and values describe plants grown during the late spring and early summer in three-gallon containers in a polyethylene-covered greenhouse in Grand Haven, Michigan and under cultural practices typical of commercial *Buddleia* production. During the production of the plants, day temperatures ranged from 18° C. to 27° C. and night temperatures ranged from 5° C. to 10° C. Plants were five years old when the photographs were taken and three years old when the description was taken. In the description, color references are made to The Royal Horticultural Society Colour Chart, 2015 Edition, except where general terms of ordinary dictionary significance are used.

Botanical classification: *Buddleia alternifolia* 'SMNBAB'.

Parentage:

*Female, or seed, parent*.—Unidentified proprietary selection of *Buddleia alternifolia*, not patented.

*Male, or pollen, parent*.—Unknown proprietary selection of *Buddleia alternifolia*, not patented.

Propagation:

*Type*.—By softwood stem cuttings.

*Time to initiate roots plant, summer*.—About 15 days at temperatures ranging from about 18° C. to 27° C.

*Time to produce a rooted plant, summer*.—About 24 days at temperatures ranging from about 18° C. to 27° C.

*Root description*.—Fine, fibrous; typically brown in color, actual color of the roots is dependent on substrate composition, water quality, fertilizer, substrate temperature and physiological age of roots.

*Rooting habit*.—Freely branching; medium density.

Plant description:

*Plant and growth habit*.—Deciduous perennial shrub; relatively compact, outwardly spreading to weeping plant habit with cascading inflorescences; vigorous growth habit; moderate to rapid growth rate; freely branching habit; dense and bushy appearance.

*Plant height*.—About 75 cm.

*Plant width* (*spread*).—About 80 cm.

*Lateral branches*.—Quantity: Freely branching habit with about ten to twelve primary lateral branches developing per plant. Length: About 40 cm to 55 cm. Diameter: About 4 mm. Internode length: About 1 cm. Strength: Strong, flexible. Aspect: About 40° to 80° from vertical. Texture: Initially, pubescent; becoming woody with development. Color, developing: Close to 144C. Color, woody: Close to 197A.

Leaf description:

*Arrangement and appearance*.—Alternate, simple.

*Length*.—About 7 cm.

*Width*.—About 1 cm.

*Shape*.—Lanceolate.

*Apex*.—Narrowly acute.

*Base*.—Attenuate.

*Margin*.—Entire.

*Texture, upper and lower surfaces*.—Slightly pubescent.

*Venation pattern*.—Pinnate.

*Color*.—Developing and fully expanded leaves, upper surface: Close to NN137B; venation, close to NN137B. Developing and fully expanded leaves, lower surface: Close to 192B; venation, close to 144C.

*Petioles*.—Length: About 3 mm. Diameter: About 1 mm. Texture, upper and lower surfaces: Sparsely pubescent. Color, upper and lower surfaces: Close to 144C.

Flower description:

*Flower type and flowering habit*.—Single salverform flowers arranged on terminal and axillary compact, rounded and dense panicles; panicles arranged along cascading lateral branches; freely flowering habit with about 50 flowers developing per panicle and about 100 to 200 panicles per lateral branch with numerous flowers developing per plant during the flowering season; flowers face upright to outwardly depending on position on the panicle.

*Fragrance*.—Moderately fragrant; sweet, pleasant.

*Natural flowering season*.—Plants flower continuously in the early summer in Michigan; individual flowers last about one to two weeks on the plant; flowers persistent.

*Flower buds*.—Height: About 8 mm. Diameter: About 1 mm. Shape: Oblong with a bulbous apex. Color: Close to N82C.

*Inflorescence length*.—About 3 cm.

*Inflorescence diameter*.—About 2.5 cm.

*Flower diameter*.—About 5 mm.

*Flower depth* (*height*).—About 1 cm.

*Throat diameter*.—About 1 mm.

*Tube length*.—About 8 mm.

*Tube diameter, proximally*.—About 1 mm.

*Petals*.—Quantity per flower: Typically four petals arranged in a single whorl fused at the base. Length: About 2 mm. Width: About 2 mm. Shape: Broadly elliptic. Apex: Obtuse. Margin: Entire. Texture, upper and lower surfaces: Smooth, glabrous; delicate. Color: Developing and fully expanded petals, upper surface: Close to N82C to N82D. Developing and fully developed petals, lower surface: Close to N82D. Throat: Close to N82C Tube: Close to N82D.

*Sepals*.—Quantity per flower: Typically four in a single whorl forming a cup-shaped calyx. Length: About 1 mm. Width: Less than 1 mm. Shape: Oblong. Apex: Obtuse. Margin: Entire. Texture, upper surface: Smooth, glabrous. Texture, lower surface: Sparsely pubescent. Color, upper and lower surfaces: Close to 192B.

*Peduncles*.—Length: About 2 cm. Diameter: About 3 mm. Strength: Strong. Angle: About 60° to 90° from the lateral branch axis. Texture: Smooth, glabrous. Color: Close to 144C.

*Pedicels*.—Length: About 2 mm. Diameter: About 1 mm. Strength: Strong. Angle: About 45° from the peduncle axis. Texture: Sparsely pubescent. Color: Close to 192B.

*Reproductive organs*.—Stamens: Quantity per flower: Typically two to four; filaments adnate to the corolla tube. Anther length: About 1 mm. Anther shape: Oblong. Anther color: Close to 162C. Pollen amount: Scarce to moderate. Pollen color: Close to 162D. Pistils: Quantity per flower: One. Pistil length: About 1 mm. Stigma shape: Oblong. Stigma color: Close to 144C. Style length: About 1 mm. Style color: Close to 144C. Ovary color: Close to 144C.

*Seeds and fruits*.—To date, seed and fruit development have not been observed on plants of the new *Buddleia*.

Pathogen & pest resistance: To date, plants of the new *Buddleia* have not been observed to be resistant to pathogens and pests common to *Buddleia* plants.

Garden performance: Plants of the new *Buddleia* have been observed to have good garden performance and tolerate rain, wind and to be suitable for USDA Hardiness Zones 4 through 9.

It is claimed:

1. A new and distinct *Buddleia* plant named 'SMNBAB' as herein illustrated and described.

* * * * *